United States Patent [19]

West

[11] Patent Number: 5,482,838

[45] Date of Patent: Jan. 9, 1996

[54] TRYPSIN-SENSITIVE AGENT ABLE TO REDUCE PAI-1 AND βAPP EXPRESSION IN SENESCENT CELLS AND INCREASE THE ABILITY OF FIBROBLASTS TO DIVIDE IN CULTURE

[75] Inventor: Michael D. West, Belmont, Calif.

[73] Assignee: Geron Corporation, Menlo Park, Calif.

[21] Appl. No.: 14,838

[22] Filed: Feb. 8, 1993

[51] Int. Cl.⁶ .............................. C12P 21/02; C07K 3/00
[52] U.S. Cl. .................. 435/70.3; 530/827; 530/350; 435/70.1; 435/948
[58] Field of Search .................................. 435/71.1, 70.1, 435/70.3; 530/827, 840, 848, 350

[56] References Cited

PUBLICATIONS

Sage, H., et al., "J. Cell Biology," vol. 97, Dec. 1988, pp. 1933–1938.
Goldstein, 249 *Science* 1129–1133, Sep. 7, 1990.
Finlay and Cristofalo, 168 *Exp. Cell Res.* 191–202, 1987.
Finlay et al, 156 *Exp. Cell Res.* 462–470, 1985.

*Primary Examiner*—Marian C. Knudde
*Assistant Examiner*—Kristin Larson
*Attorney, Agent, or Firm*—Richard J. Warburg; Amy P. Stark; Kevin Kaster

[57] ABSTRACT

Purified trypsin-sensitive agent or analog thereof, able to downregulate collagenase, PAI-1 and βAPP expression in senescent cells isolatable from culture medium having growing fibroblasts or U937 promyelocytic cells.

1 Claim, 5 Drawing Sheets

FIG. 1.

LABELLING ASSAY

Plate 2 × 10$^4$ cells per coverslip.

↓ 4 hours

Add protein in MEM, 10% FCS with Gentamicin

↓ 22 hours

Add $^3$H TdR (1uCi per coverslip)

↓ 4 hours

Fix cells, cover with photographic emulsion, expose & develop

↓

COUNT LABELLED NUCLEI
SCORE AS % LABELLED NUCLEI

TRYPSIN-SENSITIVE AGENT ABLE TO REDUCE PAI-1 AND β APP EXPRESSION IN SENESCENT CELLS AND INCREASE THE ABILITY OF FIBROBLASTS TO DIVIDE IN CULTURE

BACKGROUND OF THE INVENTION

This invention relates to agents which extend the proliferative capacity of somatic cells and reverse senescent gene expression.

The in vitro proliferative capacity of normal somatic cells is finite. This cessation of proliferation after 60–100 doublings in vitro is reproducible and is a frequently used model of aging on a cellular level (see, e.g., Hayflick and Moorehead, 25 *EXP. Cell Res.* 585, 1961; Hayflick, ibid., 37:614, 1985; West et al., 184 *Exp. Cell Res.* 138, 1989). The specific maximum proliferative capacity of a given cell strain is dependent upon the tissue of origin and is inversely proportional to the in vivo age of the donor (see, e.g., Martin et al., 23 *Lab. Invest.* 86, 1979; Goldstein et al., 64 *Proc. Natl. Acad. Sci. USA* 155, 1969; Schneider and Mitsui, ibid., 73:3584, 1976; and Le Guilty et al., 19 *Gerontologia* 303, 1973).

Various theories have been proposed to explain this cessation of proliferation including the free radical theory which suggests that free radical-mediated damage to DNA and other macromolecules is causative in critical loss of cell function (Harmon, 11 *J. Gerontol.* 298, 1956; Harmon, 16 *J. Gerontol.* 247, 1961), somatic mutation theories which propose that without genetic recombination cells lack the ability to proliferate indefinitely due to a progressive loss of genetic information (Burnet, "Intrinsic Mutagenesis—A Genetic Approach to Aging", Wile, N.Y., 1976; Hayflick, 27 *Exp. Gerontol.* 363, 1992), and genetically programmed theories of senescence which suggest that the expression of senescent-specific genes actively inhibit cell proliferation perhaps under the direction of a mitotic clock (Martin et al., 74 *Am. J. Pathol.* 137, 1974; Goldstein, 249 *Science* 1129, 1990).

Consistent with the programmed theory, some genes such as collagenase, plasminogen activator inhibitor 1 (PAI-1) and β-amyloid precursor protein (βAPP) have been demonstrated to be expressed at a higher level in senescent cells (West et al., Supra; West et al., 31 *Gerontologist* 313, 1991; West et al., *Id.* at 355). These gene products in turn are thought to play important roles in age related diseases.

Finlay and Cristofalo, 168 *Exp. Cell Res.* 191, 1987, and Finlay et al., 156 *Exp. Cell Res.* 462, 1985, describe a secondary effector molecule produced by cells exposed to glucocorticoid hormones. They indicate that chronic exposure to hydrocortisone or dexamethasone results in a 20–40% extension in the proliferative lifespan of W138 human fetal lung fibroblast cells.

Normally, W138 cells possess a limited replicative lifespan. The authors, Finlay and Cristofalo, indicate that the decline in proliferative capacity of cultures of these cells with serial subcultivation is characterized by (a) a decreased rate of growth, (b) an exponential decrease in a number of cells capable of incorporating tritiated thymidine into DNA, and (c) a decreased saturation density of the culture. The authors further indicate that addition of glucocorticoid hormone to these cells at subcultivation results in both an increase in tritiated thymidine incorporation into DNA during logarithmic growth, and a 20–40% increase in saturation density. No response was observed when glucocorticoid hormone was added during logarithmic growth instead of at subcultivation.

The stimulatory effects of glucocorticoid hormone are said to be mediated by a factor present in the medium conditioned by the cells for 24 hours following subcultivation in the presence of the hormone. This factor is said to be stable at 75° C. for 90 minutes, dialyzable using a 12,000 daltons molecular weight (MW) cut-off tubing, but retained when dialyzed against 3,500 daltons MW cut-off tubing. Increased time of dialysis using the 3,500 daltons MW tubing, however, did result in significant loss of activity. The authors state, "It is possible, therefore, that the factor(s) is of MW less than 3 500." The authors also indicate that the material is resistant to treatment with trypsin, chymotrypsin and protease, and is relatively polar. Finally, the authors indicate, "[I]t appears that peptide components are not present in the stimulatory refractor. If the glucocorticoid-induced factor is a small peptide or glycopeptide, then the peptide components necessary for the stimulatory activity are either not available for proteolytic attack or are not cleaved by the endopeptidases used in this study." (168 *Exp. Cell Res.* 191, 1987)

SUMMARY OF THE INVENTION

The present invention relates to the purification of a trypsin sensitive agent which is active to increase the number of cell doublings of fetal lung or neonatal skin fibroblasts, compared to cells grown in the absence of the agent. In addition, the agent is able to down-regulate expression of collagenase and PAI-1 expression in senescence cells, and is isolatable from culture medium in which fibroblasts or U937 promyelocytic cells are grown. The agent is also able to down-regulate expression of βAPP (beta amyloid precursor protein) and may downregulate heparin sulfate proteoglycan (HSPG) and β-1,trypsin (ACT). Finally, the agent is also able to stimulate DNA synthesis in senescent fibroblasts and endothelial cells.

Applicant has determined that a novel group of agents, e.g., one termed GE1428, can be readily purified by techniques described herein, and are useful for many therapeutic and prophylactic methods which treat or prevent various pathologic conditions associated with cellular senescence or senescent gene expression. These conditions include atherosclerosis, vascular endothelial senescence, connective tissue senescence and cellular senescence of various somatic cells. Specific conditions also include connective tissue atrophy, osteoarthritis, age-related macular degeneration, Alzheimer's disease and thrombosis. Thus, the invention features pharmaceutical compositions and therapeutic agents useful for treatment of these diseases, and methods for use of those pharmaceutical agents. The invention also features a method for screening for other factors which have similar properties to those of the exemplified agent, and for providing analogues of the exemplified agent.

Thus, in a first aspect, the invention features a purified trypsin sensitive agent or analog thereof, able to downregulate collagenase and PAI-1 expression in a senescent cell. The agent is isolatable from culture medium in which growing fibroblasts or U937 promyelocytic cells are present.

By "purified" is meant that the agent is separated from the environment in which it naturally occurs, or from one or more components of that natural environment. Most preferably, the agent is separated from all cellular components with which it naturally occurs, and is provided as a homogeneous solution or powder suitable for administration to an animal, such as a human. The term includes not only an agent isolated from medium in which cells are growing, but also agents produced using recombinant DNA methodology, or other molecular biology techniques to cause expression of the agent from cells containing DNA encoding that agent.

By "trypsin sensitive" is simply meant that the agent is cleaved by trypsin, and thereby loses some or all of its biological activities, particularly those related to downregulation of collagenase and PAI-1 expression in a senescent cell.

By "analog" is meant an agent which is homologous at the amino acid sequence or nucleotide base sequence level with that exemplified in this application. These analogues can be isolated from the same or different cells as those described below, or may be created using recombinant DNA methodology. Those of ordinary skill in the art will recognize that the purified agent described below can be used to clone genes encoding that agent. For example, the amino acid sequence of the agent can be determined either by N-terminal analysis (or by enzymatic digestion followed by N-terminal analysis of the enzyme fragments) to provide a crude amino acid sequence of that agent. This amino acid sequence can then be used to develop selective oligonucleotides which can be used as genetic probes in a library, e.g., a cDNA library. Such a cDNA library may be produced from messenger RNA expressed after treatment of cells with dexamethasone. In this way, an appropriate clone can be isolated, and its DNA sequence determined. This clone will encode an agent of the present invention.

Those of ordinary skill in the art will recognize that variations in one or more codons of such a gene can be readily made, which will not influence the amino acid sequence of the agent produced from that clone. In addition, amino acid substitutions can be made in areas of the protein, which are not necessary for biological activity. Such areas are readily screened using the assays described in this application, by site-specific mutagenesis techniques, or by providing deletion mutants of that clone. Each of the mutants which has the desired biological activity is an analog of the present invention. In addition, the clone can be used to screen for homologous or complementary nucleotide base sequences in other organisms, which clones can then be isolated using standard molecular biology techniques. Those clones can then be screened to determine those which express the desired biological activity.

Amino acid substitutions can also be made in non-conserved regions, i.e., those not required for biological activity. Preferably, such substitutions are conservative or non-conservative. For example, glycine may be substituted for valine, or positively charged amino acids for other such amino acids.

By "downregulation" is meant that the expression of one or more genes is reduced compared to normal levels. An example of an experiment by which such downregulation can be determined is provided below. Those of ordinary skill in the art will recognize that this term is used in its normal scientific manner, and that other experiments can be used to measure such downregulation.

By "senescent cell" is meant a cell which has lost its ability to divide under normal proliferative conditions. That is, the cell has reached that point described by Hayflick and Moorehead, 25 *Experimental Cell Research* 585, 1961, which is functionally defined as the limited capacity of that cell to divide beyond a finite number of population doublings. More specifically, the term includes the loss of ability of the cell to replicate in the presence of normally appropriate replicative signals. The term does not include quiescent cells which might be induced to replicate under appropriate conditions. Thus, such senescent cells are those cells which have reached the end of mortality stage 1 (M–1) described by Shay et al., 27 *Experimental Gerontology;* 477, 1992. In this invention, such cells may be cause to proliferate or divide beyond the number of cell divisions characteristic of a non-used (untreated) cell's M–1 period.

In preferred embodiments, the purified agent is also able to downregulate expression of β-amyloid protein expression in astrocytes, and may also downregulate expression of HSPG and ACT in such cells. The agent also stimulates DNA synthesis in senescent fibroblasts and endothelial cells, and increases the number of cell doublings compared to cells grown in the absence of the agent. The over expression of collagenase, PAI-1, and βAPP may play an important role in the pathogenesis of osteoarthritis, vascular thrombosis, and Alzheimer's disease, respectively. Therefore, this agent may have important therapeutic applications.

In a related aspect, the invention features a pharmaceutical composition having a therapeutically effective amount of an agent as described above. By "therapeutically effective amount" is meant that amount of agent which is necessary to provide a reversal, or partial reversal, of a deleterious phenotype associated with a disease or condition to be treated. This phrase is a well-recognized phrase, and the amount actually applied in treatment will be dependent upon the individual animal to which treatment is to be effected. Preferably, the amount is optimized such that any side effects which may be caused by the agent are avoided, to the extent possible.

In a further aspect, the invention features a method for use of the above agents or therapeutic compositions for treatment of diseases or conditions associated with senescent gene expression, the presence of senescent cells, or any condition which would benefit from prolongation of the ability of cells to divide on the reversal of senescent gene expression. Such conditions include those noted above, and in particular, connective tissue atrophy, osteoarthritis, Alzheimer's disease and thrombotic conditions. The method involves administering the agent in a therapeutically effective amount to the individual affected by the disease or condition.

In yet another aspect, the invention features a method for screening for factors which downregulate the expression of collagenase and/or PAI-1, and βAPP. The method involves contacting a potentially useful factor with a cell which expresses collagenase or PAI-1, and determining whether such expression is reduced below normal levels.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of an assay useful for determining the effect of agents on replicative senescence.

AGENTS

Figure 2:
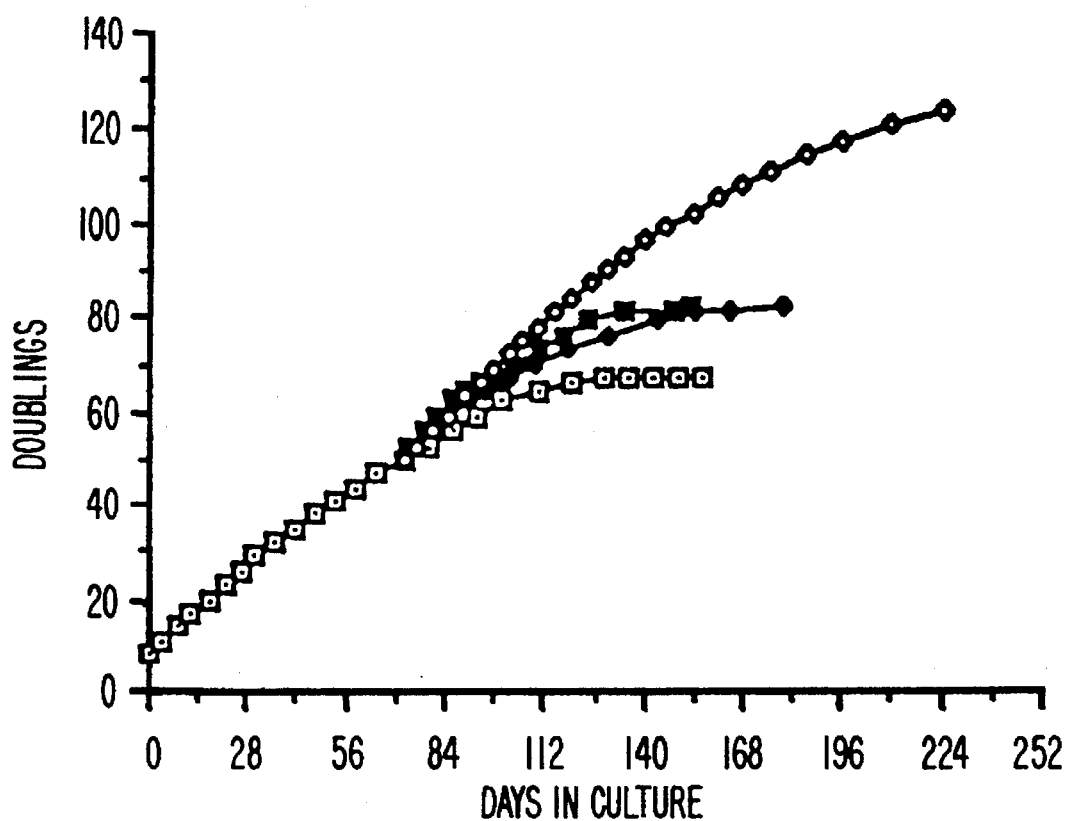
FIG. 2 is a graphical representation of the effect of an agent of the present invention on fibroblast cell doubling.

Agents of the present invention are generally described above. There follows a non-limiting example of one exemplary agent of the present invention which can be isolated in highly purified form from conditioned media in which cultured fibroblasts or U937 promyelocytic cells are grown. Other cellular sources may also be used for production of such an agent.

As noted above, analogues of agents of the present invention can be isolated using techniques described in this application, or by screening clone libraries for complementary or other DNA. Those of ordinary skill in the art will recognize other equivalent methods for isolating such analogues. These agents, unlike the hormones which cause their production (e.g., hydrocortisone and dexamethasone), are therapeutically useful and have activity without the side effects associated with such hormones. For example, the hormones are associated with mediation of gene expression which may accelerate aging, and thus cause diseases such as osteoporosis or aging of skin (Lehman et al., 81 *J. Invest. Dermatol.* 169, 1983). In addition, agents of the present invention are active at all stages of cell growth, unlike steroid hormones which appear to have their effect only in relatively young cells. Unlike some growth factors, such as TGF-β, agents of the present invention downregulate the expression of PAI-1 and thus have greater use in treatment of disease associated with cellular senescence.

COMPOSITIONS

Compositions or products according to the invention may conveniently be provided in the form of solutions suitable for parenteral, nasal, intraocular or oral administration. In many cases, it will be convenient to provide an agent in a single solution for administration.

If the agents are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The agents of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of agent which will be effective in one or multiple doses to perform a desired function. As will be recognized by those in the field, an effective amount of therapeutic agent will vary with many factors including the age and weight of the patient, the patient's physical condition, the blood sugar level to be obtained, and other factors.

ADMINISTRATION

Selected agents, e.g., GE1428 can be administered prophylactically, or to patients suffering from a target disease, e.g., by exogenous delivery of the agent to an afflicted tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with such agents and/or delivery of oligonucleotides expressing such agents are also suitable, and can be constructed and administered using standard procedures.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular uptake, regardless of the delivery vehicle or strategy. Such assays will also determine the intracellular localization of the agent following uptake, ultimately establishing the requirements for maintenance of steady-state concentrations within the appropriate cellular compartment. Efficacy and cytotoxicity can then be tested. Toxicity will not only include cell viability but also cell function.

Some methods of delivery, e.g., for GE1428, that may be used include:

a. encapsulation in liposomes, b. transduction by retroviral vectors, and c. conjugation with cholesterol.

At least three types of delivery strategies are useful in the present invention, including: agent modifications, particle carrier drug delivery vehicles, and retroviral expression vectors. Unmodified agents may be taken up by cells. To enhance cellular uptake, the agent may be modified essentially at random, in ways which reduces its charge but maintains specific functional groups. This results in a molecule which is able to diffuse across the cell membrane, thus removing the permeability barrier.

Modification of agents to reduce charge is just one approach to enhance the cellular uptake of these molecules. The structural requirements necessary to maintain agent activity are well understood by those in the art. These requirements are taken into consideration when designing modifications to enhance cellular delivery. The modifications are also designed to reduce susceptibility to enzymatic degradation. Both of these characteristics should greatly improve the efficacy of the agent.

Intravenous administration with a drug carrier designed to increase the circulation half-life of the agent can be used. The size and composition of the drug carrier restricts rapid clearance from the blood stream. The carrier, made to accumulate at the site of disease, can protect the agent from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver agents to cells and that the agent remains biologically active.

For example, a liposome delivery vehicle originally designed as a research tool, LIPOFECTIN, liposome delivery vehicle, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents and protein-based pharmaceuticals.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the affected cells. Chemical modification of the agent to neutralize negative or positive charges may be all that is required for penetration. However, in the event that charge neutralization is insufficient, the modified agent can be co-formulated with permeability enhancers, such as AZONE, permeability enhancer, or oleic acid, in a liposome. The liposomes can either represent a slow release presentation vehicle in which the modified agent and permeability enhancer transfer from the liposome into the targeted cell, or the liposome phospholipids can participate directly with the modified agent and permeability enhancer in facilitating cellular delivery. In some cases, both the agent and permeability enhancer can be formulated into a suppository formulation for slow release.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the agent to an accessible diseased or other tissue. Subcutaneous administration drains into a localized lymph node which proceeds through the lymphatic network into the circulation. The rate of entry into the circulation has been shown to be a function of molecular weight or size. The use of a liposome or other drug carrier localizes the agent at the lymph node. The agent can be modified to diffuse into the cell, or the liposome can directly participate in the delivery of either the unmodified or modified agent to the cell.

Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 10–2000 mg/kg of body weight/day. The duration of treatment will extend through the course of the disease symptoms, usually at least 14–16 days and possibly continuously. Multiple daily doses are anticipated for topical applications, ocular applications and CNS applications. The number of doses will depend upon disease delivery vehicle and efficacy data from clinical trials.

Establishment of therapeutic levels of agent within the target cell is dependent upon the rate of uptake and degradation. Decreasing the degree of degradation will prolong the intracellular half-life of the agent. Thus, chemically modified agents, e.g., GE1428, may require different dosaging.

EXAMPLE 1

GE1428

One agent of the present invention is termed GE1428 and can be isolated from cells stimulated with glucocorticoid hormones, such as hydrocortisone and dexamethasone.

GE1428 can be isolated from the conditioned medium of fibroblasts treated with 0.2 μm dexamethasone during replating following trypsinization. Expression of GE1428 is transient; GE1428 appears to be expressed during cell attachment since it is observed only during the 24 hours following replating. Other cells, such as the promyelocytic cell line U937, when induced by phorbol ester to differentiate from a cell that grows in suspension into an attached macrophage-like cell can also be used to isolate this agent.

Specifically, the fibroblasts were plated at a subconfluent density of $2\times10^4$ cells/cm$^2$ in 12, 850 cm$^2$ roller bottles with 50 ml of standard MEM medium supplemented with 10% fetal bovine serum and 0.2 Jun dexamethasone. After 24 hours, the medium was removed and clarified by centrifugation for 15 minutes at 3,500×g. The conditioned medium was then dialyzed 3× against 100 volumes of MEM medium at 4° C. over a period of 24 hours using 3,500 dalton MW cutoff dialysis membrane. Protein was then precipitated by bringing the conditioned medium to 60% ammonium sulfate and centrifuging at 15,000×g for 20 minutes. The pellet was then resuspended in 1.0 ml phosphate buffered saline and passed over a SEPHACRYL, Sepharose gel S-200 column. Fractions were collected and assayed for their ability to stimulate DNA synthesis in senescent cells by the method shown in FIG. 1. In one experiment, GE1428 eluted in fractions 101–104 of 0.5 ml fractions.

Referring to FIG. 1, about $2\times10^4$ senescent cells were plated on a coverslip and 4 hours later treated with a sample potentially including the desired agent in MEM, 10% Fetal calf serum (FCS) and Gentamycin. Twenty-two hours later, tritiated thymidine was added (1 µCi per coverslip) and 4 hours later the cells were fixed, immersed in photographic emulsion and incubated 24 hours at 37° C. The coverslip was developed and the percentage of nuclei with silver grains scored. If the desired agent was present, there was an increase in labeled nuclei.

Fractions displaying activity to stimulate DNA synthesis in senescent cells were then pooled and precipitated with 60% ammonium sulfate. The pellet was resuspended in phosphate-buffered saline (PBS), applied to a C18 HPLC column, and separated with an acetonitrile gradient. Fractions (e.g., 5–7 of 200 µl aliquots) showing the ability to stimulate DNA synthesis in senescent cells were pooled, dialyzed as above 3× against 100× volumes of MEM at 4° C. over 24 hours. Aliquots were then quick frozen and stored at –20° C. This procedure provides a single band on a polyacrylamide gel, showing that GE1428 is pure and homogenous, with a MW of 3.5–4.5 KD.

In another method, the same procedure can be used with U937 promyelocytic cells plated in the same medium with 10% FBS and 0.2 µm dexamethasone and 100 nm phorbol myristate acetate.

EXAMPLE 2

Rescue from Fibroblast Senescence

Referring to FIG. 2, human forearm fibroblasts were grown in MEM supplemented with 10% Fetal bovine serum and the following supplements: GE1428—1 ng/ml every 3 days PBS vehicle; 13-cis-Retinoic acid—100 ng/ml every 3 days PBS vehicle; Dexamethasone—0.2 µM every 3 days 1000× dilution from 1 mM stock in ethanol; Control—equal volume PBS.

The results are shown in FIG. 2. Without agent, the cells senescence (as shown by lack of cell division) at about 70 doublings. With dexamethasone or retinoic acid, some further cell divisions occur, but with an agent of this invention cell doublings (at least 120 compared to 70 for the control) continue for a significant period of time (at least 224 days compared to 112 days for the control). Thus, an agent of this invention increases the ability of fibroblasts to divide in culture.

Biological Activity of Agent

Evidence is provided herein that GE1428 reverses senescent gene expression in at least two cell types, namely, connective tissue fibroblasts, and brain astrocytes. Such reversal of senescent gene expression in connective tissue fibroblasts is beneficial in the treatment of age-related degenerative joint disease and other such diseases characterized by cellular senescence.

The agent also increases replicative potential of cultured fibroblasts, endothelial cells, and astroglial cells and is thus useful in diseases caused by senescence of such cells. The following examples illustrate these biological activities.

EXAMPLE 3

Downregulation of PAI-1

Figure 3:
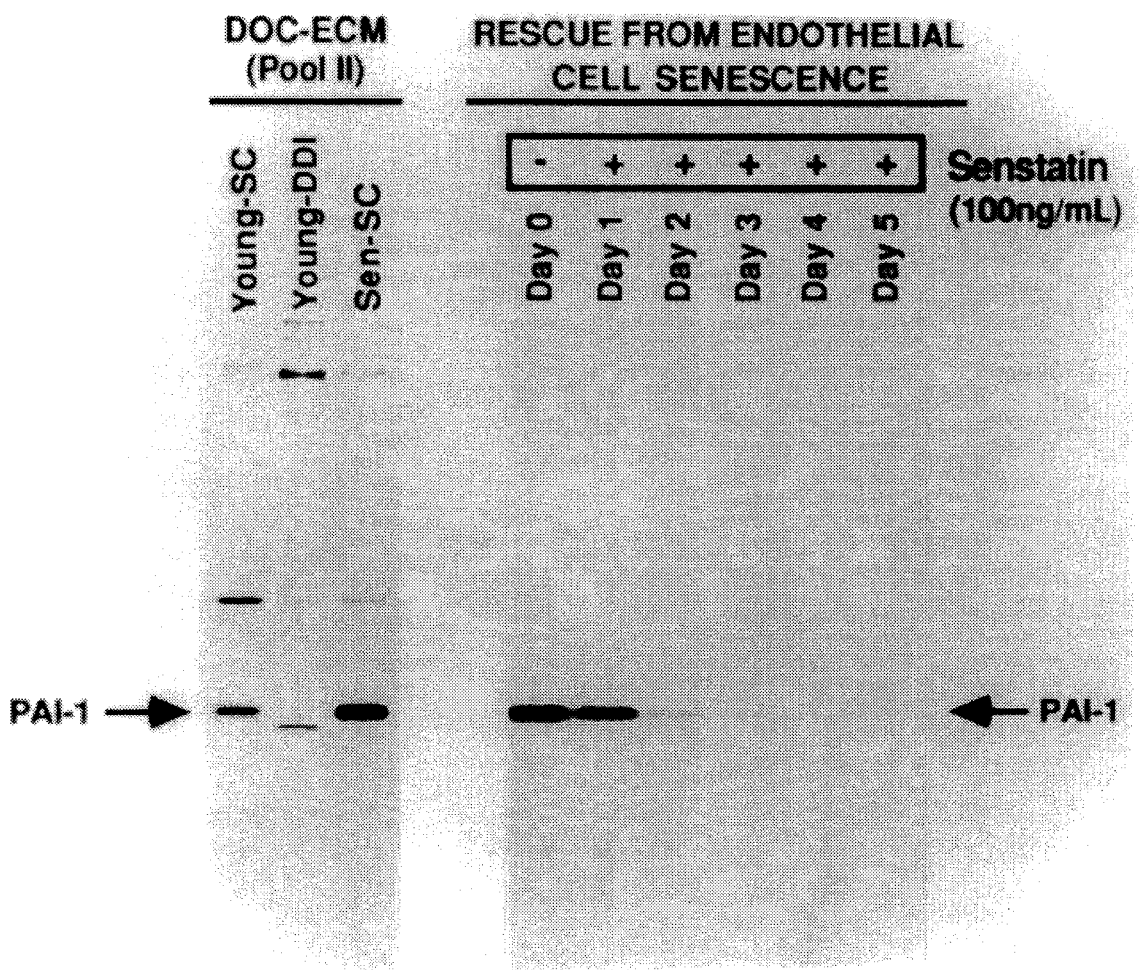
FIG. 3 is a copy of an autoradiogram showing elevated PAI-1 secretion by senescent lung fibroblasts and downregulation of PAI-1 by senescent cells after treatment with GE-1428.

Plasminogen activator inhibitor 1 (PAI-1) is overexpressed by senescent human lung fibroblasts. Referring to FIG. 3 (left-hand side), cells were incubated for 2 hours in methionine-free medium supplemented with 50 µCi/ml of $^{35}$S-methionine. Deoxycholate—insoluble extracellular matrix was then prepared by standard procedures. Radiolabeled extracellular matrix protein was then analyzed by PAGE and autoradiography. Young-SC=young subconfluent 2 days with 10% FCS. Young-DDI=young with density-dependent inhibition of growth cultured 5 days 0.5% FCS. Sen-SC=senescent subconfluent 2 days 10% FCS. These data show that PAI-1 is expressed at a greater level in senescent cells.

Referring to FIG. 3 (right-hand side), senescent cells prepared in the manner described above were pretreated with 100 ng/ml of GE1428. The data shows that GE1428 downregulates PAI-1 expression.

EXAMPLE 4

Downregulation of βAPP

Figure 4:
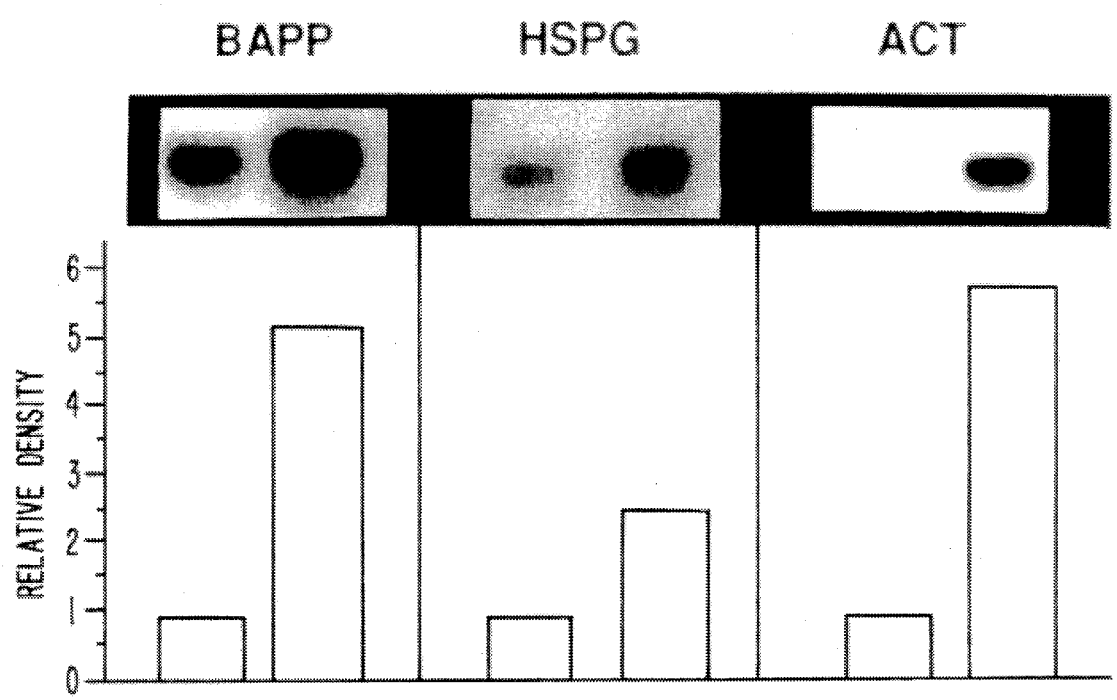
FIG. 4 is a histogram (below) showing expression of genes believed to participate in Alzheimer's disease in young and senescent astrocytes, and a Northern blot illustrating such expression (above).

Referring to FIG. 4, senescent brain astrocytes provide a useful in vitro model of Alzheimer's disease. As shown in the figure, senescent human brain astrocytes (PD36) show increased expression of mRNA for precursors of amyloid plaques of Alzheimer's disease, namely, βAPP, HSPG and ACT.

Figure 5:
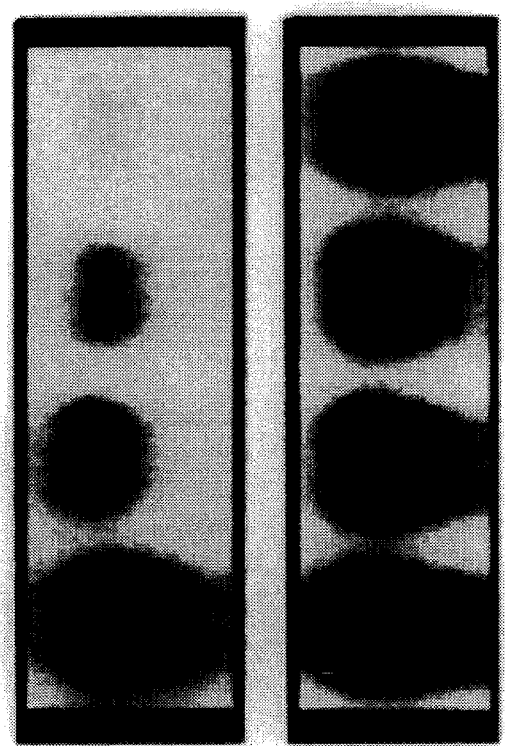
FIG. 5 is a reproduction of an autoradiogram of a Northern blot of the expression of βAPP expression after treatment with or without an agent of the present invention.

Referring to FIG. 5, senescent human brain astrocytes were treated with either GE1428 to a final concentration of 100 ng/ml in PBS, or with an equal volume of PBS. Cells were harvested at 0, 12, 24, and 48 hours following treatment, and mRNA was harvested according to standard techniques. Ten µg of poly(A) RNA was then loaded on a formaldehyde denaturing gel, electrophoresed, blotted to nitrocellulose and hybridized to a βAPP cDNA probe. The filter was washed, autoradiographed, and scanned with relative density scored relative to untreated cells. The data shows that GE1428 causes reduced expression of βAPP, thus evidencing downregulation of βAPP in senescent astrocytes.

Other embodiments are within the following claims.

I claim:

1. Purified trypsin-sensitive agent GE 1428, wherein said agent reduces PAI-1 expression in senescent human lung fibroblasts and βAPP expression in senescent human brain astrocytes, and increases the ability of human forearm fibroblasts to divide in culture, and wherein said agent is isolated from culture medium wherein said culture medium contains growing fibroblasts or U937 promyelocytic cells, and wherein said agent has a MW of 3.5–4.5 kD.

* * * * *